US009224203B2

(12) United States Patent　　(10) Patent No.: US 9,224,203 B2
Sakaue　　(45) Date of Patent: Dec. 29, 2015

(54) MEDICAL IMAGE INFORMATION SYSTEM AND MEDICAL IMAGE PROCESSING SERVER

(71) Applicants: Kabushiki Kaisha Toshiba, Minato-ku (JP); Toshiba Medical Systems Corporation, Otawara (JP)

(72) Inventor: Kousuke Sakaue, Nasushiobara (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/243,448

(22) Filed: Apr. 2, 2014

(65) Prior Publication Data

US 2014/0233815 A1　　Aug. 21, 2014

Related U.S. Application Data

(63) Continuation of application No. PCT/JP2014/000230, filed on Jan. 17, 2014.

(30) Foreign Application Priority Data

Jan. 18, 2013　(JP) .................................. 2013-007501

(51) Int. Cl.
*G06T 7/00*　　(2006.01)
*G06Q 50/24*　　(2012.01)
*G06F 19/00*　　(2011.01)

(52) U.S. Cl.
CPC ............ *G06T 7/0012* (2013.01); *G06F 19/321* (2013.01); *G06Q 50/24* (2013.01); *G06T 2207/30004* (2013.01)

(58) Field of Classification Search
CPC ................... G06Q 50/24; G06F 19/321; G06T 2207/30004; G06T 7/0012
See application file for complete search history.

(56) References Cited

U.S. PATENT DOCUMENTS 7,852,948 B2　12/2010　Suzuki
2008/0021834 A1 *　1/2008　Holla et al. ..................... 705/51
(Continued)

FOREIGN PATENT DOCUMENTS

JP　　2006006449 A　*　1/2006
JP　　2006-333254 A　　12/2006
(Continued)

OTHER PUBLICATIONS

International Search Report issued on Feb. 10, 2014 for PCT/JP2014/000230 filed on Jan. 17, 2014 with English Translation of Categories.

(Continued)

*Primary Examiner* — Bhavesh Mehta
*Assistant Examiner* — Pinalben Patel
(74) *Attorney, Agent, or Firm* — Oblon, McClelland, Maier & Neustadt, L.L.P

(57) ABSTRACT

A medical image information system of an embodiment includes: a terminal device and a medical image processing server connected via a network, wherein the medical image processing server includes a medical image storage unit in which a medical image is stored, and an image processing unit that generates, from the medical image, a display screen and display screen information based on a request from the terminal device to transmit to the terminal device, and the image processing unit includes a speed-lowering determination unit that determines, based on either related information of a medical image or connection status of the terminal device or both, a setting item pertaining to a wait process for lowering a transmission timing of a result of image processing, and a speed-lowering processing unit that carries out a wait process for lowering a transmission timing of the display image based on the setting item.

9 Claims, 11 Drawing Sheets

(56) References Cited

U.S. PATENT DOCUMENTS

| | | | |
|---|---|---|---|
| 2010/0131873 A1* | 5/2010 | Mejia et al. | 715/764 |
| 2013/0129165 A1* | 5/2013 | Dekel et al. | 382/128 |
| 2013/0138717 A1* | 5/2013 | Lingley | 709/203 |

FOREIGN PATENT DOCUMENTS

| | | |
|---|---|---|
| JP | 2011-30108 A | 2/2011 |
| JP | 2012-65814 A | 4/2012 |

OTHER PUBLICATIONS

International Written Opinion mailed on Feb. 10, 2014 for PCT/JP2014/000230 filed on Jan. 17, 2014.

Hiroshi Fukatsu, et al., "Thin Client System", Eizojoho Medical, vol. 43, No. 9, Aug. 1, 2011, pp. 708-713.

* cited by examiner

FIG.3

| Operation input type | Speed-lowering setting item | Speed-lowering setting value |
|---|---|---|
| Displaying of forward frame-by-frame playback | Communication wait time | 1 second |
| Displaying of reverse frame-by-frame playback | Communication wait time | 1 second |
| Forward-feed cine-displaying | Cine-displaying fps value | 5 fps |
| Reverse-feed cine-displaying | Cine-displaying fps value | 5 fps |

FIG.4

| Operation input type | Speed-lowering setting item | Speed-lowering setting value |
|---|---|---|
| Displaying of forward frame-by-frame playback | Communication wait time | 0 second |
| Displaying of reverse frame-by-frame playback | Communication wait time | 0 second |
| Forward-feed cine-displaying | Cine-displaying fps value | 30 fps |
| Reverse-feed cine-displaying | Cine-displaying fps value | 30 fps |

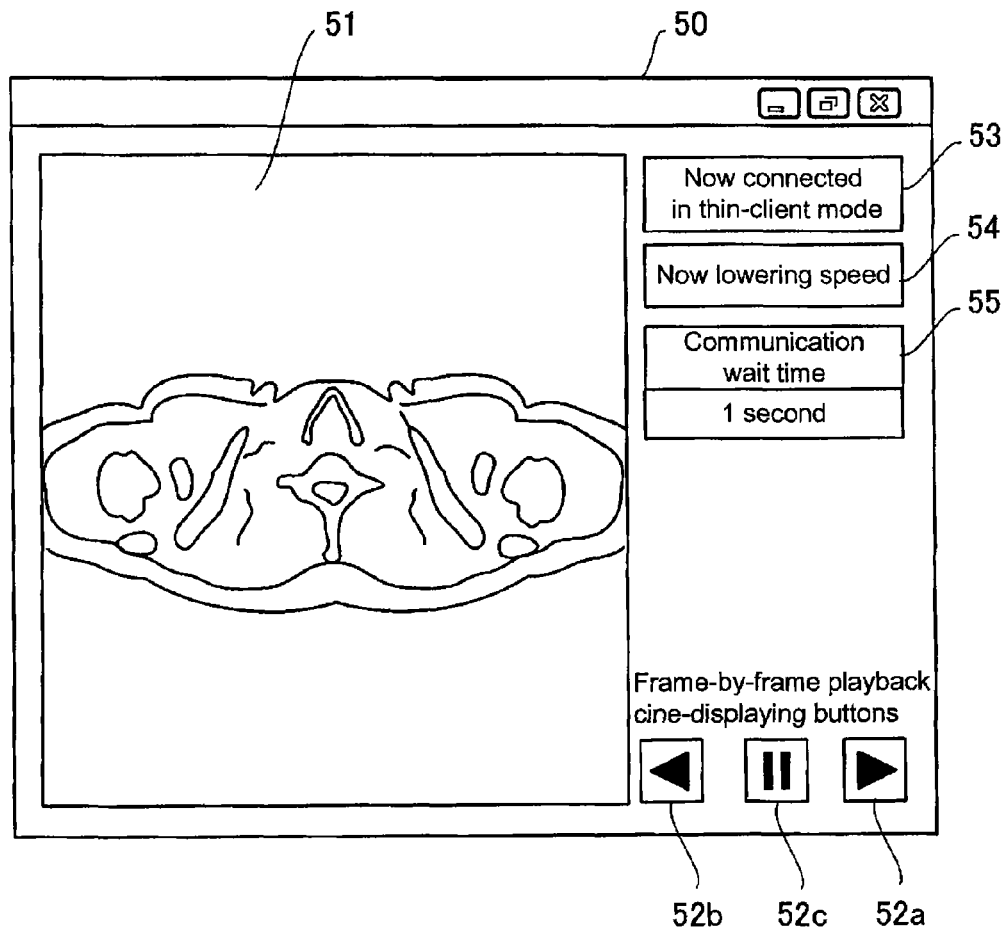

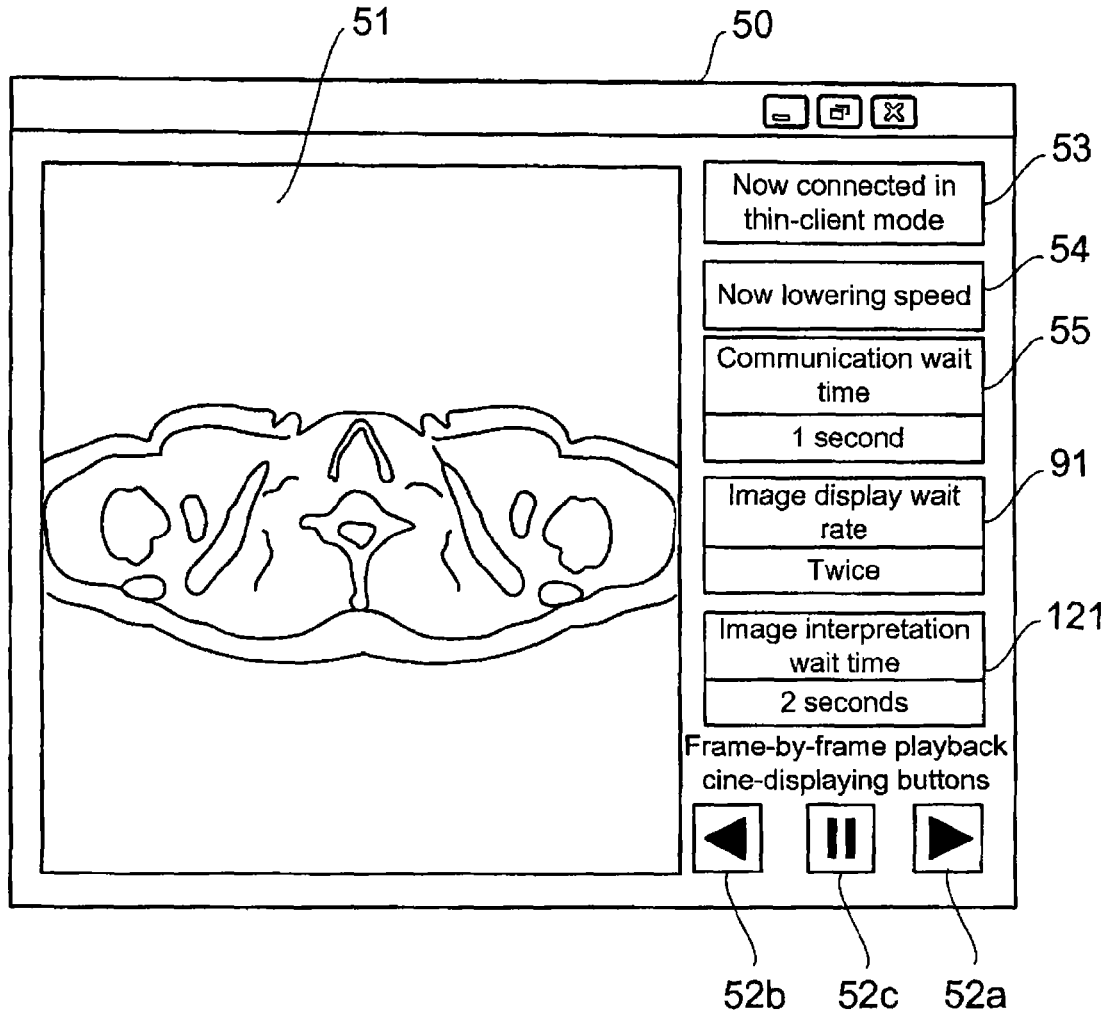

MEDICAL IMAGE INFORMATION SYSTEM AND MEDICAL IMAGE PROCESSING SERVER

CROSS-REFERENCE TO RELATED APPLICATION

This application is a continuation of International Application No. PCT/JP2014/000230, filed on Jan. 17, 2014, which is based upon and claims the benefit of priority from the prior Japanese Patent application No. 2013-007501, filed on Jan. 18, 2013, the entire contents of which are incorporated herein by reference.

FIELD

Embodiments of the present invention relates to a medical image information system and medical image processing server that are used for interpreting a medical image and performing any other operation.

BACKGROUND

Conventionally, to use a medical image information system, application software, such as those of image processing and image viewing, need to be installed on each terminal, and settings such as security measures need to be performed. The management of such a stand-alone terminal comes with problems such as how to lighten the burden of maintenance, ensure security, and reduce costs. In recent years, the computing technology of servers has advanced; the thin-client technology, which allows application software to be executed intensively on servers, is expected to be one of effective steps taken to address the problems.

Meanwhile, in the case of the thin-client technology, images are displayed via a network, thereby raising concerns of restraints on display performance and function and the like for remote image interpretation. If this thin-client technology is applied to medical image information systems such as those for remote image interpretation, the systems would be likely to be affected by line bandwidths and delay. In particular, when medical images that are relatively large in transfer capacity are cine-displayed (or when each piece of slice information is sequentially image-displayed as if the images are moving pictures), the deterioration of the display performance and dropping frames may occur, affecting the operation by doctors of interpreting the images.

Conventional techniques have been proposed to solve the above problems by changing the size of medical images or by partially transferring the medical images. Moreover, to detect dropping frames, there is a technique by which a client is synchronized with a server to calculate a difference between a medical image received by the client and image information transmitted by the server.

However, to achieve accurate interpretation of images, it is necessary to stop a drop in the image display performance and to prevent the dropping of frames. Accordingly, one embodiment of the present invention is intended to solve the above problems, and to provide a medical image diagnosis information system that prevents a drop in the image display performance and the dropping of frames.

BRIEF DESCRIPTION OF THE DRAWINGS

FIG. 3 is an example of a table of speed-lowering setting items when a thin client is connected, according to the same embodiment.

FIG. 4 is an example of a table of speed-lowering setting items when a console is connected, according to the same embodiment.

FIG. 5 is an example of a screen displayed on a terminal of the medical image information system according to the same embodiment.

FIG. 12 is an example of a screen displayed on a terminal of a medical image information system according to the same embodiment.

FIG. 13 is an example of how an image interpretation wait time is set according to the same embodiment.

DETAILED DESCRIPTION

Figure 1:
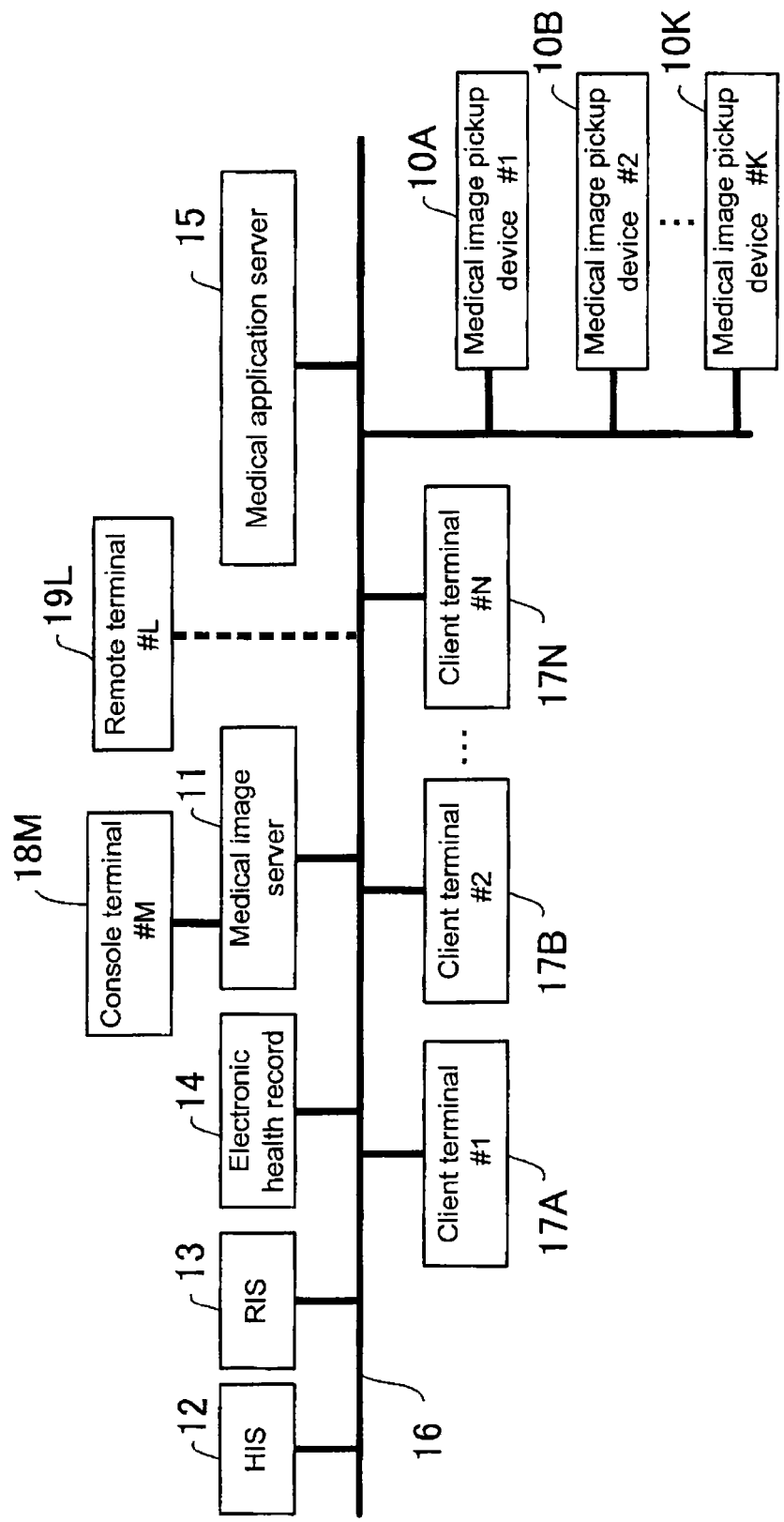
FIG. 1 is a network configuration diagram of a medical image information system according to the present embodiment.

A medical image information system of one embodiment of the present invention includes: a terminal device that is connected via a network; and a medical image processing server that carries out image processing based on a request from the terminal device and transmits a result thereof to the terminal device, wherein the medical image processing server includes a medical image storage unit in which a medical image is stored, and an image processing unit that generates, from the medical image, a display screen and display screen information based on a request from the terminal device to transmit to the terminal device, and the image processing unit includes a speed-lowering determination unit that determines, based on either related information of a medical image or connection status of the terminal device or both, a setting item pertaining to a wait process for lowering a transmission timing of a result of image processing, and a speed-lowering processing unit that carries out a wait process for lowering a transmission timing of the display image based on the setting item.

Moreover, a medical image processing server of the embodiment that is connected to a terminal device via a network includes: a medical image storage unit in which a medical image is stored, and an image processing unit that generates, from the medical image, a display screen and display screen information based on a request from the terminal device to transmit to the terminal device, wherein the image processing unit includes a speed-lowering determination unit that determines, based on related information of the medical image, a setting item pertaining to a wait process for lowering a transmission timing of a result of image processing, and a speed-lowering processing unit that carries out a wait process for lowering a transmission timing of the display image based on the setting item.

Furthermore, a medical image processing server of the embodiment that is connected to a terminal device via a network includes: a medical image storage unit in which a medical image is stored, and an image processing unit that generates, from the medical image, a display screen and display screen information based on a request from the terminal device to transmit to the terminal device, wherein the image processing unit includes a connection condition detection unit that detects status of connection to the terminal device, a speed-lowering determination unit that determines, based on the connection status, a setting item pertaining to a wait process for lowering a transmission timing of a result of image processing, and a speed-lowering processing unit that carries out a wait process for lowering a transmission timing of the display image based on the setting item.

Hereinafter, embodiments for carrying out the invention will be described in detail with reference to FIGS. 1 to 13.

A medical image information system of the present embodiment is made by adding functions into a medical image server (PACS: Picture Archiving and Communication Systems) or a medical application server through software and hardware. The medical image information system can be so configured as to work closely with systems such as HIS (Hospital Information System), RIS (Radiology Information System), an electronic health record system, and a medical image pickup device (modality). The medical image information system can easily achieve consistency with existing systems.

First Embodiment

As shown in FIG. 1, a medical image information system to which the present embodiment is applied is built on a network 16 to which the following devices are connected: a plurality of medical image pickup devices 10A, 10B, ... 10K such as an ultrasonic diagnosis device, a CT (Computed Tomography) device, and a MRI (Magnetic Resonance Imaging) device; a medical image processing server (e.g. PACS) 11 in which data of medical images taken by the medical image pickup devices 10K (Reference symbol 10K represents a plurality of medical image pickup devices connected) is stored; a hospital information system (HIS) 12; a radiology information system (RIS) 13; an electronic health record system 14; and a medical application server 15. The medical image information system includes a plurality of client terminals 17A, 17B, ... 17N that image interpretation doctors use to log in to the medical image processing server 11.

To the medical image processing server 11, console terminals 18M (Reference symbol 18M represents a plurality of console terminals) are directly connected. Remote terminals 19L (Reference symbol 19L represents a plurality of remote terminals) that are placed in a remote location can be connected to the network 16 to access the medical image processing server 11.

According to the present embodiment, what is described is a case where the medical image processing server 11 and client terminals 17A, 17B, ... 17N make up a thin-client system. The same can be applied to those having a server function, such as the medical application server 15 and the medical image pickup devices 10K.

The thin client means a system in which, while the client terminals 17N (Reference symbol 17N represents a plurality of client terminals connected) only perform as few processes as possible, most of processes, including image processing, are carried out by the medical image processing server 11 or the medical application server 15. An image interpretation doctor uses a mouse, keyboard, and other devices connected to the client terminal 17N for inputting of image operation, and can carry out image interpretation for transferring and outputting of a screen processed by the medical image processing server 11.

Figure 2:
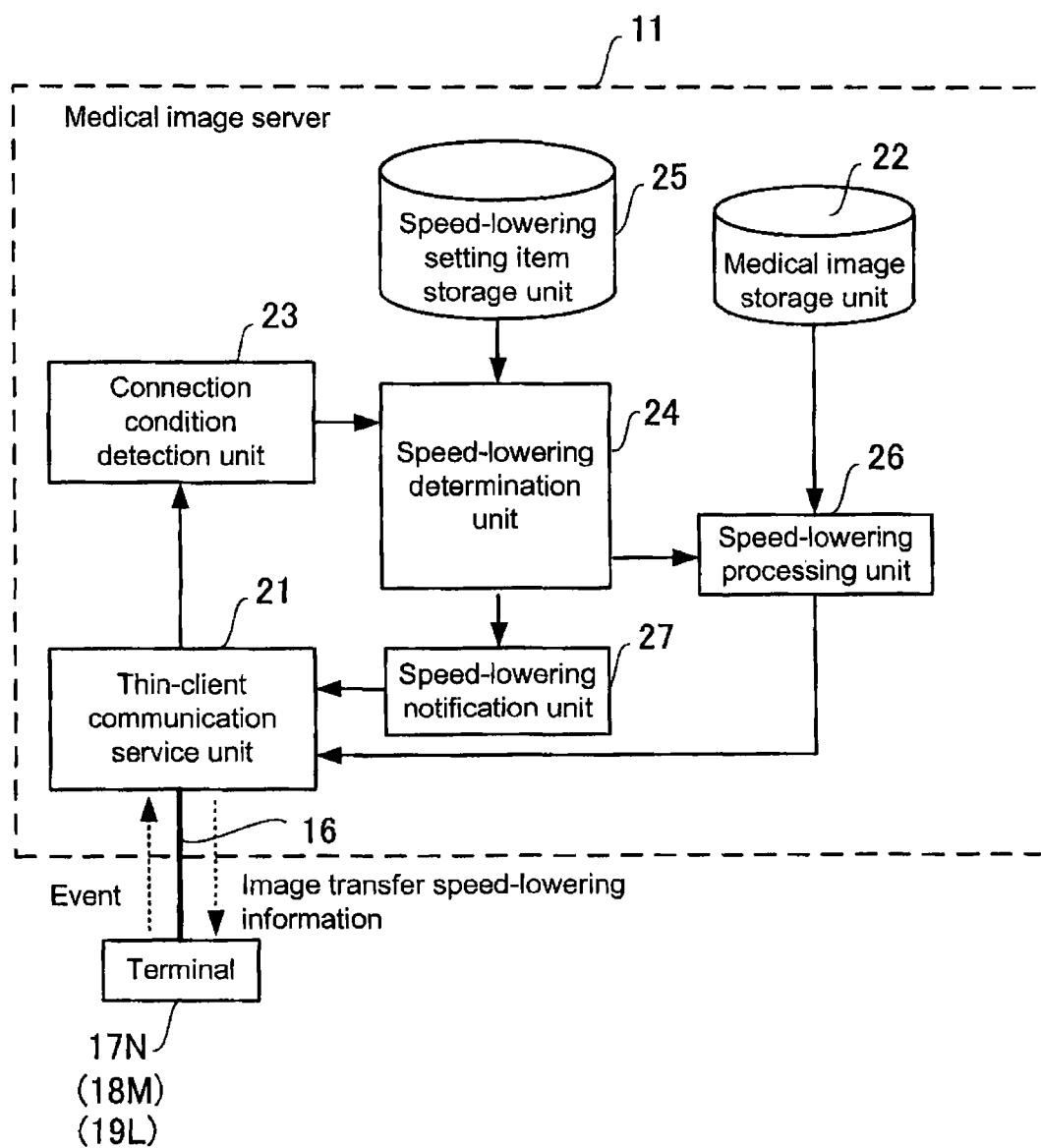
FIG. 2 is a configuration diagram of blocks of a medical image processing server according to a first embodiment.

The block configuration of the medical image processing server 11 of the present embodiment will be described with reference to FIG. 2. The present embodiment is characterized by a process of lowering a speed of a screen transfer response at a time when the inputting of image operation, such as displaying of continuous frame-by-frame playback or cine-displaying, is carried out: The inputting of image operation is a relatively heavy load on the network 16.

The medical image processing server 11 includes a thin-client communication service unit 21, a medical image storage unit 22, a connection condition detection unit 23, a speed-lowering determination unit 24, a speed-lowering setting item storage unit 25, a speed-lowering processing unit 26, and a speed-lowering notification unit 27.

The thin-client communication service unit 21 communicates, via the network 16, with the terminals 17N, 18M, and 19L (The client terminals, the console terminals, and the remote terminals are referred to as terminals). As indicated by dotted-line arrows, image operation input information of an image interpretation doctor is transmitted from the terminals 17N, 18M, and 19L as an event. The medical image processing server 11 reads a medical image from the medical image storage unit 22, and performs image processing corresponding to the inputting of image operation to obtain a screen, and transfers the screen to a terminal. Speed-lowering information, such as speed-lowering setting items of image processing which are performed at the time of the transferring of the screen, is simultaneously displayed within a transfer screen. The thin-client communication service unit 21 also operates a communication service of OS (Operation System) running on the medical image processing server 11.

The connection condition detection unit 23 makes an inquiry to the thin-client communication service unit 21 to determine whether the connection condition detection unit 23 is connected to the terminals 17N (or 18M, 19L) in a thin-client manner. Based on information that is obtained by using API (Application Program Interface) offered by a thin client service of OS, commands, and the like, the type of connection status is determined, such as whether individual terminals are being connected in a thin-client manner. For example, if the thin-client connection is realized by connection in Remote Desktop Protocol, the determination can be made by obtaining session information thereof or by performing any other operation. Not only is the thin-client connection determined, but other types of connection status, such as console connection by which the terminals are directly connected to the medical image processing server 11, and remote connection, are determined. It is more desirable that the determination be made by acquiring the type of connection status of a communication protocol used for the connection.

The speed-lowering determination unit 24 determines, based on the results of determination by the connection condition detection unit 23 and speed-lowering setting items stored in the speed-lowering setting item storage unit 25, whether to lower a speed of a response to the inputting of image operations including displaying of frame-by-frame playback, cine-displaying, and the like. According to the present embodiment, during the thin-client connection, the speed-lowering determination unit 24 determines to lower the speed of a response to all the displaying of frame-by-frame playback and cine-displaying. However, the speed-lowering determination unit 24 may individually determine whether to lower the speed of a response to the inputting of image operations depending on the type of the thin client service, the type of the inputting of image operation, an image operation amount, or the like, as described later.

In the speed-lowering setting item storage unit 25, by the type of the inputting of image operations, which include the displaying of frame-by-frame playback among other things, the speed-lowering setting items that are used for lowering the speed of a response to the inputting of image operations, speed-lowering setting values thereof, and the like are stored. For example, a table shown in FIG. 3 is stored.

FIG. 3 is an example of a table of speed-lowering setting items when a thin client is connected. The types of the inputting of image operations include: "displaying of forward frame-by-frame playback," "displaying of reverse frame-by-frame playback," "forward-feed cine-displaying", and "reverse-feed cine-displaying." A speed-lowering setting item for the inputting of image operations "displaying of forward frame-by-frame playback" and "displaying of reverse frame-by-frame playback" is a "communication wait time" whose speed-lowering setting value is 1 second. A speed-lowering setting item for the inputting of image operations "forward-feed cine-displaying", and "reverse-feed cine-displaying" is a "cine-displaying fps value" whose speed-lowering setting value is 5 fps (frames per second). The values of the speed-lowering setting values vary according to the resolution of a transmitted screen or the like.

Meanwhile, when the console terminal 18M is a terminal connected to the medical image processing server 11, the speed of a response to the inputting of image operation is not lowered because the connection is not established in a thin-client manner. FIG. 4 is an example of a table of speed-lowering setting items when a console is connected. That is, a "communication wait time" for the inputting of image operations "displaying of forward frame-by-frame playback" and "displaying of reverse frame-by-frame playback" is set to 0 second. A "cine-displaying fps value" for the inputting of image operations "forward-feed cine-displaying", and "reverse-feed cine-displaying" is set to a normal value or 30 fps. In this manner, settings are made in such a way as not to lower the speed.

The speed-lowering processing unit 26 executes the process of lowering the speed of a display image response to the inputting of image operation based on the type of connection status and the speed-lowering setting items.

FIG. 5 shows an example of a screen displayed on the terminal 17N (or 18M, 19L). On a display screen 50 that is transferred from the medical image processing server 11, various kinds of display screen information are displayed, including not just a medical image 51 that is to be interpreted but also speed-lowering setting items. An image interpretation doctor interprets the image by operating frame-by-frame playback/cine-displaying buttons 52. For example, when the doctor wants to perform "forward frame-by-frame playback/forward-feed cine-displaying," the doctor presses the button 52a. When the doctor wants to perform "reverse frame-by-frame playback/reverse-feed cine-displaying," the doctor presses the button 52b. To stop the "cine-displaying," the doctor presses the button 52c.

Information 53 displayed indicates a current connection status. In this example, the information 53 indicates that the connection is established in a thin client mode. Information 54 displayed indicates that the process of lowering the speed of an image operation input response is under way. During the process of lowering the speed, information 55 displayed includes a speed-lowering setting item that is currently executed for the inputting of image operation, and a speed-lowering setting value.

Figure 6:
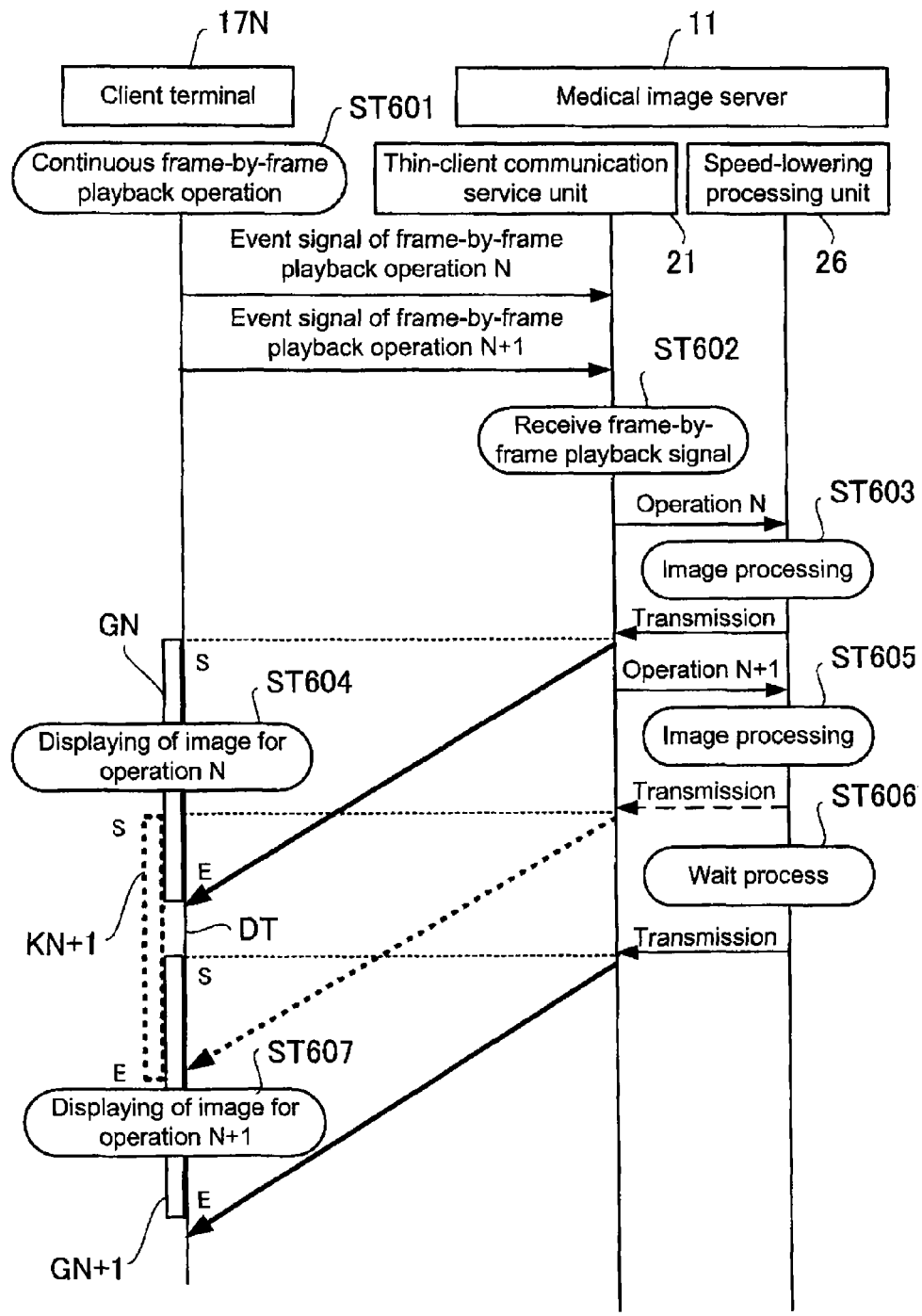
FIG. 6 is a sequence chart between a terminal and a medical image processing server according to the same embodiment.

FIG. 6 is a sequence chart performed between the client terminal 17N and the medical image processing server 11. The sequence of a case where the inputting of image operation of continuous "frame-by-frame playback displaying" is carried out will be described with reference to FIG. 6. At step ST601, an image interpretation doctor performs a continuous frame-by-frame playback operation of a medical image through the client terminal 17N that is connected in a thin-client mode. At this time, a frame-by-frame playback displaying operation event signal is transmitted from the terminal 17N to the thin-client communication service unit 21 of the medical image processing server 11. In order to carry out discussions by generalizing the "continuous frame-by-frame playback operation," an integer N will be used, and an event signal of frame-by-frame playback operation N and an event signal of frame-by-frame playback operation N+1 will be successively transmitted.

At step ST602, the thin-client communication service unit 21 receives the event signals of frame-by-frame playback operation that are transmitted successively. At step ST603, image processing is started for the operation N. If the operation N is performed at the beginning or after a certain period of time has passed, then a display screen is transmitted immediately after the image processing is ended.

At step ST604, an image for the operation N is displayed on the client terminal 17N. At this time, if the bandwidth of a communication line secured is insufficient, and a communication delay or the like is relatively large, it takes time for the client terminal 17N to display the image. In this case, the time consumed by the displaying of the image is represented by S to E of quadrilateral GN.

At step ST605, following the transmitting of the display screen for the operation N, image processing is started for operation N+1. At this time, in the case of a frame-by-frame playback signal N+1 that is successively transmitted, a display screen is not immediately transmitted, and a wait process (step ST606) is performed to lower the speed of a response for the above-described speed-lowering setting item. As indicated by dotted-line arrow and dotted-line quadrilateral KN+1, if a wait process is not performed before a display screen is transmitted, the displaying of the display screen for the operation N+1 will start before the displaying of the image for the operation N is ended. Therefore, some of images may disappear, and the dropping of frames may occur in some cases.

At step ST607, as an appropriate wait measure is taken at step ST606, the timing of the screen displaying of the operation N does not overlap with the timing of the screen displaying of the operation N+1. Therefore, it is possible to prevent some of the images from disappearing, and to prevent the dropping of frames. Moreover, the time DT between the displaying of the screen for the operation N and the displaying of the screen for the operation N+1 (or between E of the quadrilateral GN and S of the quadrilateral GN+1) is the time for an image interpretation doctor to interpret a medical image displayed on the terminal. For the time DT between the displaying of the screen for the operation N and the displaying of the screen for the operation N+1, an appropriate image interpretation time can be set, as described later.

Figure 7:
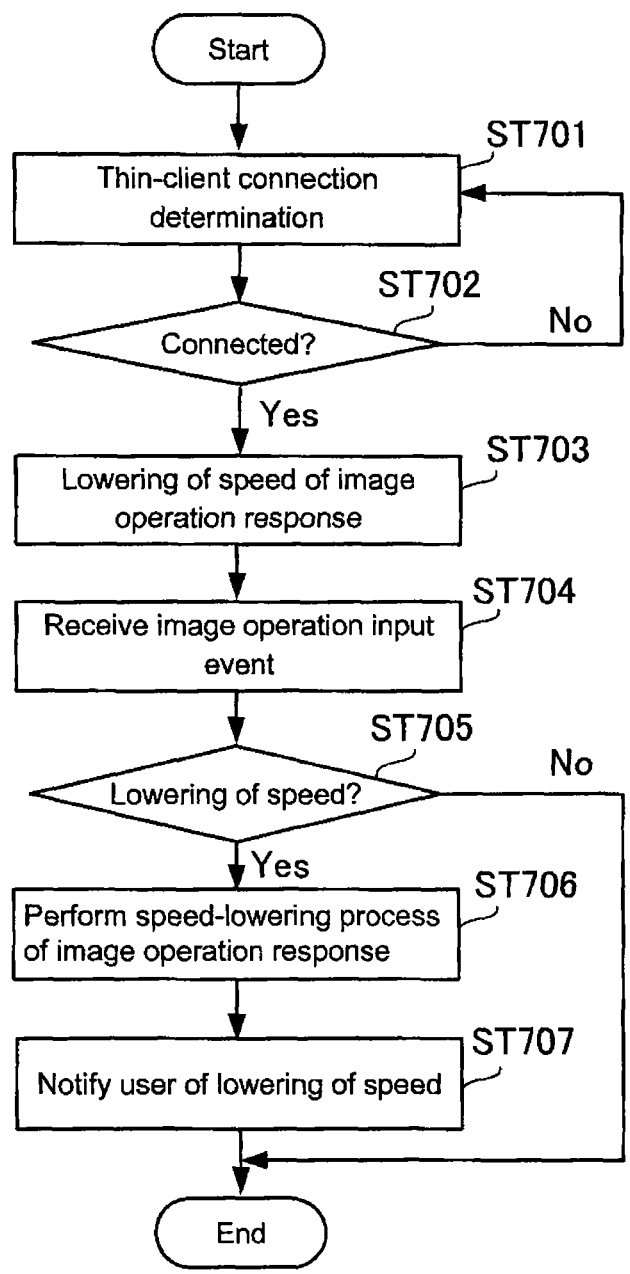
FIG. 7 is a flowchart illustrating an operation of the medical image information system according to the same embodiment.

The operation of the medical image information system having the above configuration will be described with reference to a flowchart of FIG. 7. At step ST701, the connection condition detection unit 23 makes a thin-client connection determination.

At step ST702, a determination is made as to whether the type of connection status is a thin-client connection. If it is determined that the type of connection status is a thin-client connection (ST702: Yes), the process proceeds to an image operation response speed-lowering determination at step ST703. If it is determined that the type of connection status is not a thin-client connection (ST702: No), the process returns to step ST701 to continue a connection status type determination, or the process may make an image operation response speed-lowering determination of step ST703 depending on the type of each connection status.

At Step ST703, the speed-lowering determination unit 24 determines to lower the speed of an image operation response by following a speed-lowering setting item that is defined for each type of connection status. At step ST704, the thin-client communication service unit 21 receives an event signal of the inputting of image operation.

At step ST705, a determination is made as to lowering the speed of a response to an image operation input. For example, if the above-described successive image operation inputs are received (ST705: Yes), the process of lowering the speed is carried out (Step ST706). If non-successive image operation inputs are received such as those at the beginning (ST705: No), the process is ended without lowering the speed of a response for the image operation input. Incidentally, the speed may not be lowered for volume-type image data, which is so large in image capacity that it takes time to generate an image, and the like, as described later.

At step ST707, when the process of lowering the speed of a response to the image operation input is under way, the speed-lowering notification unit 27 displays, on the display screen 50, the fact that the process of lowering the speed of a response to the image operation input is going on for the terminal 17N, thereby issuing a warning to the image interpretation doctor.

As described above, according to the first embodiment, if a drop in line bandwidth or an increase in communication delay occurs during the thin-client connection, for example, only the speed of a response to the inputting of image operation that can be a relatively large communication load such as continuous frame-by-frame playback or cine-displaying is lowered. As a result, the image can be interpreted in a highly reliable manner, because it is possible to prevent the disappearing of some of the images and the dropping of frames.

Furthermore, the lowering of the speed of image operation inputs can be achieved by adding an application function to the medical image processing server. Therefore, there is no need to add a new function to the terminals. Thus, it is possible to achieve the following advantageous effects: it is possible to reduce the burden of maintenance, ensure security, and reduce costs.

Second Embodiment

According to the first embodiment, as for the lowering of the speed of a response to the inputting of image operation, a decision is made by making a determination as to the type of connection status such as whether the connection status is a thin-client connection. According to the present embodiment, the type of connection status is determined more carefully. For example, the contrast and resolution of the display screen and the like are taken into account.

Figure 8:
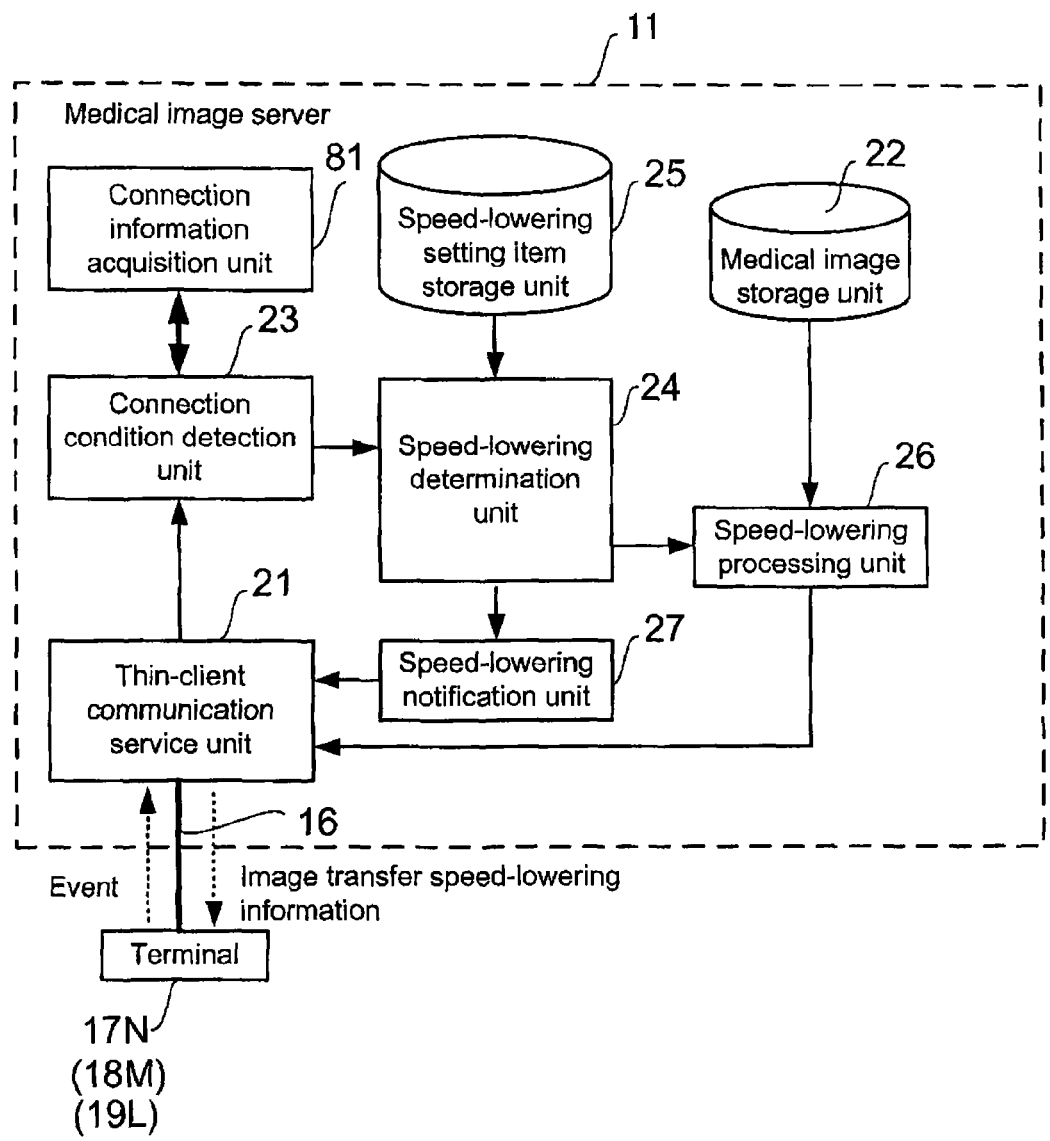
FIG. 8 is a configuration diagram of blocks of a medical image processing server according to a second embodiment.

FIG. 8 is a configuration diagram of blocks of a medical image processing server according to the second embodiment. In addition those shown in FIG. 1, a connection information acquisition unit 81 is added. The connection information acquisition unit 81 acquires information at the time of connection, such as the bandwidth of a communication line, a communication delay, the number of terminals connected, a CPU used for a terminal, an image display condition, and display resolution of a terminal. Depending on the acquired information, the connection information acquisition unit 81 lowers the speed of a response to the inputting of image operations, such as frame-by-frame playback operation.

More specifically, an inquiry is made to the thin-client communication service unit 21 about the bandwidth of a communication line of the network 16, a communication delay, and the number of terminals connected; or the bandwidth of a communication line of the network 16, a communication delay, and the number of terminals connected can be acquired from network connection information between the medical image processing server and the terminals 17N (18M, 19L). For example, the bandwidth of a communication line and a communication delay can be acquired by utilizing a time stamp of ICMP (Internet Control Message Protocol) protocol or a response time of a Ping command. The number of terminals connected can be acquired by checking services connected to ports.

In the wait process (Step ST606) shown in FIG. 6, by monitoring the state of communication that changes every moment and by taking those information into account, it is possible to change an optimal value of a speed-lowering setting value in real time.

Furthermore, image wait values are provided for the performance/type of a CPU used in a terminal, display conditions for a to-be-displayed medical image, display resolution, and the like. The medical-image display conditions include, for example, image display parameters WW (Window Width)/WL (Window Level) such as contrast. The medical-image display conditions are acquired from setting information of the medical image information system.

To get the type of a CPU used in the terminal 17N or the display resolution of the terminal 17N, an inquiry is made to the thin-client communication service unit 21. Alternatively, the system information may be acquired directly from the terminal 17N in advance.

Figure 9:
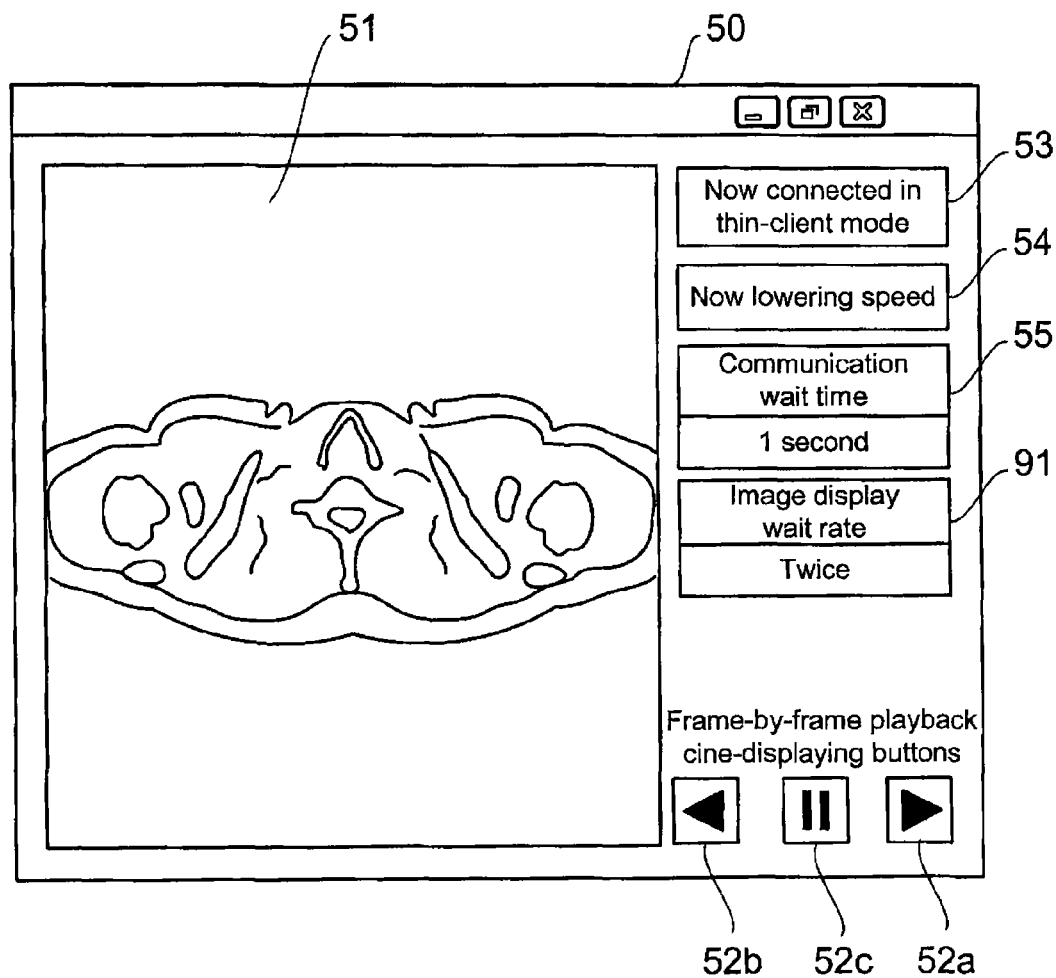
FIG. 9 is an example of a screen displayed on a terminal of the medical image information system according to the same embodiment.

FIG. 9 is an example of a screen displayed on a terminal of the medical image information system. As shown in FIG. 9, in addition to those in FIG. 5, information 91 displayed shows an image display wait rate that is currently used. The image display wait rate is displayed as a ratio with respect to a communication wait time.

Figure 10:
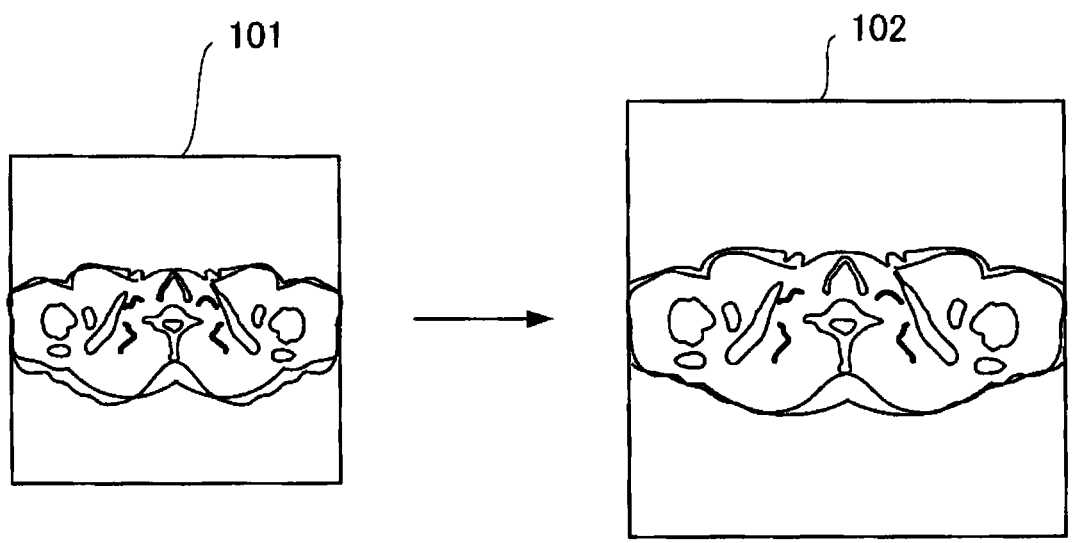
FIG. 10 is an explanatory diagram of relationship between the number of pixels displayed and an image display wait rate according to the same embodiment.

For example, as shown in FIG. 10, suppose that the number of pixels of a display screen 102 is twice the number of pixels of a display screen 101. In the case of the same communication bandwidth, what is set is twice the image display wait rate. For the image display wait rate of FIG. 9, "twice" is displayed. In this case, if the communication wait time that is set for the display screen 101 is 1 second, the total wait time for the display screen 102 is 2 seconds because the time is multiplied by the image display wait rate. As the number of terminals connected increases, the image display wait rate rises.

As described above, according to the second embodiment, if the bandwidth of a communication line is narrow, or if the communication delay is large, or if the number of terminals connected is large, or if the CPU used is running at low speed, or if the brightness of display condition is high, or if the display resolution is large, the speed is lowered with the above information taken into account. In this manner, depending on a to-be-displayed medical image and a communication state, an optimal speed-lowering setting value can be determined more carefully.

Third Embodiment

According to the present embodiment, what is described is the lowering of the speed based on a response of an image operation input with a diagnosis time, such as a diagnosis time for interpreting an image, taken into account. In this case, for example, levels of lowering the speed with respect to a response speed of an image operation input are classified by medical image-related information such as: (1) disease information; (2) checkup information; (3) an operation status of a user; and (4) supplementary information of an image. Then, a wait processing time for a speed-lowering response is changed.

Figure 11:
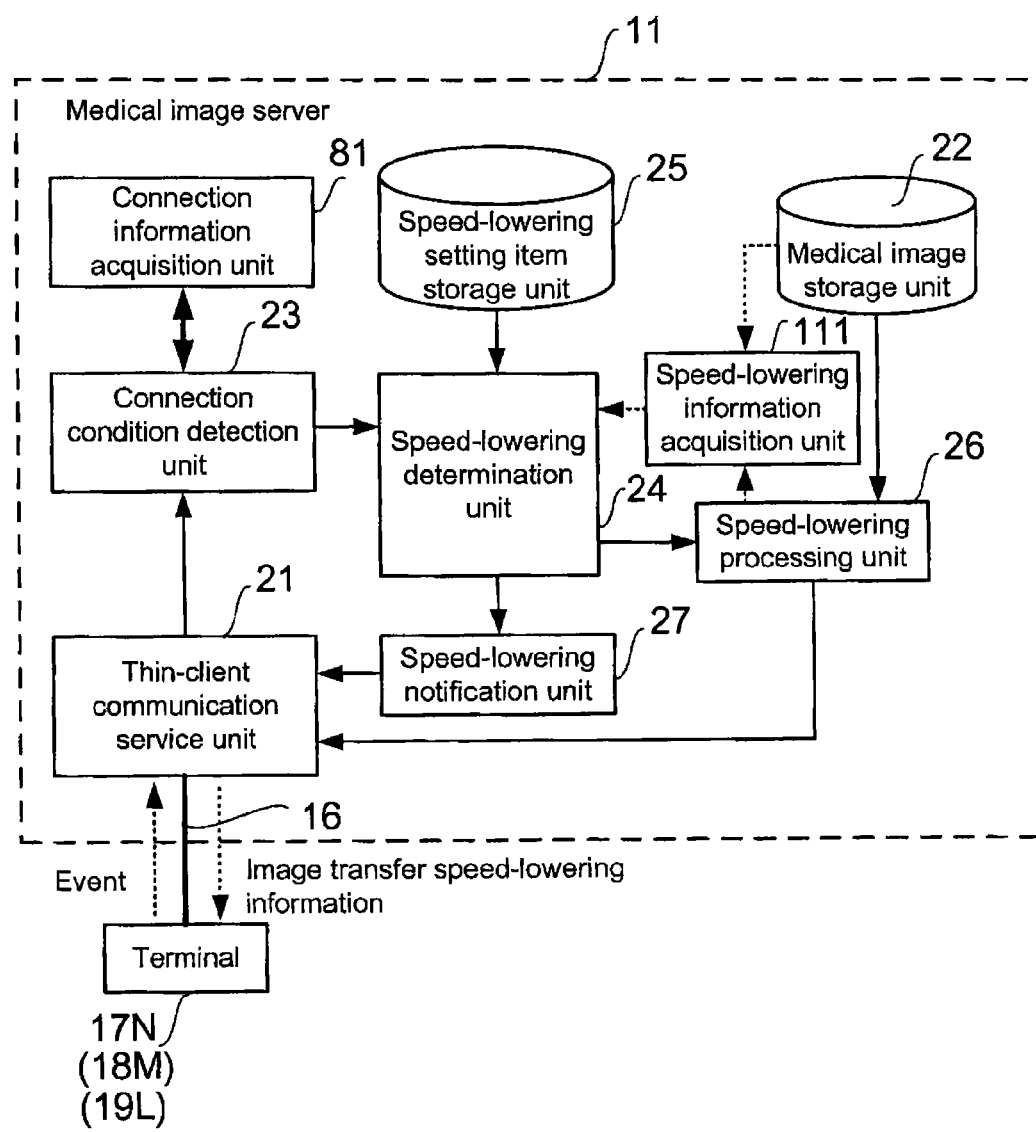
FIG. 11 is a configuration diagram of blocks of a medical image processing server according to a third embodiment.

FIG. 11 is a configuration diagram of blocks of a medical image processing server according to a third embodiment. In addition to those shown in FIG. 8, a speed-lowering information acquisition unit 111 is added. The speed-lowering information acquisition unit 111 acquires the disease information and supplementary information of a medical image from the medical image storage unit 22, and the like. The speed-lowering information acquisition unit 111 also acquires the checkup information from the electronic health record system 14, a checkup order of the HIS 12, and the like. Furthermore, by taking into account a history of image operations performed based on an image operation input event signal generated by operation of a mouse or keyboard, and the like, it is possible to realize an appropriate speed-lowering response to image diagnosis such as image interpretation. The speed-lowering determination unit 24 uses the information of the speed-lowering information acquisition unit 111 to determine the level of the speed-lowering response.

Here, the time for the wait process necessary for image diagnosis is referred to as an image interpretation wait time. In the case of FIG. 6, the image interpretation wait time is the time DT between the end point E of the image displaying for the operation N and the image display start point S for the operation N+1. Accordingly, the wait process at step ST606 makes a speed-lowering response to the inputting of image operation using a total wait time, which is calculated by adding the communication wait time and the image interpretation wait time. Incidentally, the image display wait rate described in the embodiment is taken into account, too.

FIG. 12 is an example of a screen displayed on a terminal of the medical image information system according to the present embodiment. In addition to those shown in FIG. 9, information 121 displayed shows an image interpretation wait time.

The "disease information" is information about whether the disease is of a hyperacute phase (urgency/emergency). A determination is made as to whether the disease is of a hyperacute phase (urgency/emergency); depending on the degree of urgency and the like, the image interpretation time is classified by the speed-lowering level, and is adjusted. In a normal photographing checkup, an appropriate, sufficient image interpretation time is set, and the speed-lowering level is increased. As a result, it is possible to spend a sufficient time interpreting an image. Therefore, it is possible to prevent the dropping of frames and realize the interpretation of the image. Moreover, a different image interpretation wait time can be set for image-interpretation sites.

However, in an urgent situation or any other situation, the speed sometimes should be prioritized over the dropping of some frames. In this case, the speed-lowering level may be relaxed. More specifically, the image interpretation wait time may not be set, or the image interpretation wait time may be set to a negative value in such a way as to cancel the communication wait time. In this manner, it is possible not to perform the wait process at all.

The "checkup information" is information about which medical image pickup device (modality) 10K has been used to take an image. In a volume photographing-type checkup such as those with a CT device, the amount of image data is large. However, in a simple photographing-type checkup such as X-ray photographing, the amount of data is relatively small. Therefore, based on the amounts of image data and the like, the level of the speed-lowering response is set. In the case of the volume photographing-type checkup image data, the image interpretation wait time may be set to a negative value in such a way as to cancel the communication wait time, thereby tolerating the dropping of some frames.

The "operation status of a user" is information about an operation procedure of an image operation input performed by an image interpretation doctor at a terminal. For example, in cases such as when a frame-by-frame playback operation is quickly performed or when there is less switching operation for frame-by-frame playback, the speed-lowering level may be relaxed. Meanwhile, in cases such as when a frame-by-frame playback operation is slowly performed or when there is more switching operation, it is determined that a doctor needs more image-interpretation time to carefully watch, and the level of the speed-lowering response is so set as to increase the speed-lowering level.

The setting of the speed-lowering level depending on the "supplementary information of an image" is effective for a case where an annotated medical image is interpreted again, or for any other case, for example. Around an area of an image with less annotations, the speed-lowering level is relaxed. Around an area of an image with more annotations, the speed-lowering level is increased. The speed-lowering level is determined dynamically. For example, suppose that 300 CT images are fed in order from the first CT image. When the process of feeding the images in order is started, the speed-lowering level is relaxed and the speed is prioritized when there are less annotations. Then, for example, if the $100^{th}$ image comes with annotations, the speed-lowering level is increased for frames of the images (e.g. the $90^{th}$ to $110^{th}$ images) before and after the $100^{th}$ image, thereby making the image interpretation time longer. After the $110^{th}$ image, the speed-lowering level is relaxed again to prioritize the speed. For example, if the image interpretation doctor takes notice of something on the images after the $200^{th}$ image, and if the doctor performs a "switching" operation to return to and check again the images before and after the $200^{th}$ image after viewing the images in order up to the $210^{th}$ image, the speed-lowering information acquisition unit 111 detects the "switching" operation and increases the speed-lowering level. If a forward-feed operation continues for a while after the "switching" operation is ended, the speed-lowering level may be relaxed again to prioritize the speed.

As the image interpretation wait time, a standard image interpretation time, which is determined for an image interpretation site, may be set. Moreover, in the case of a regular checkup in which the interpretation of images is conducted a predetermined number of times during a predetermined number of days, an average image interpretation time may be calculated and set.

FIG. 13 shows an example of the image interpretation wait time. For the "forward-feed" and "forward-feed cine-displaying," the image interpretation wait time is set to 2 seconds. For the "reverse-feed" and "reverse-feed cine-displaying," the image interpretation wait time is set to 4 seconds or the like. Therefore, it is possible to achieve the following advantageous effects: it is possible to set an appropriate image interpretation time for a medical image, and to complete a determined image interpretation work within almost a planned period.

Furthermore, in the case of remote terminals or the like, the communication state and the number of terminals connected change with every moment; in this case, it may take time to determine the communication wait time. In such a case, the image interpretation wait time absorbs a change in the communication wait time, and can function as a buffer time to prevent the dropping of frames.

As described above, according to the third embodiment, in addition to the communication wait time that is determined according to the communication state, the image interpretation wait time that is appropriately determined with respect to a medical image and an image interpretation state of a medical image can be set. Therefore, it is possible to make a highly reliable image diagnosis while preventing the dropping of frames.

According to the present embodiment, if a drop in line bandwidth or an increase in communication delay occurs during the thin-client connection, only the speed of a response to the inputting of image operation that can be a large communication load such as continuous frame-by-frame playback or cine-displaying is lowered. Therefore, it is possible to prevent the disappearing of some of the images and the dropping of frames. This speed-lowering response of the inputting of image operation does not limit the image processing and the transfer speed of communication on the medical image processing server. Therefore, it is possible to make maximum use of the performance of the medical image processing server. Moreover, the above advantageous effects can achieved by adding an application function only to the medical image processing server. Therefore, there is no need to add a new function to the terminals, thereby preventing adverse effects on the communication line, such as congestion. Furthermore, it is possible to achieve the following advantageous effects: it is possible to reduce the burden of maintenance, ensure security, and reduce costs.

Moreover, in addition to the wait time that varies depending on the communication state, an appropriate wait time, too, can be set for different conditions, such as sites of a medical image and an image interpretation state. Therefore, it is possible to make a highly reliable image diagnosis while preventing the dropping of frames.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and sprit of the inventions.

What is claimed is:

1. A medical image processing server that is connected to a terminal device via a network, comprising:
a medical image storage unit in which a medical image is stored; and
an image processing unit that generates, from the medical image, a display screen and display screen information based on a request from the terminal device to transmit to the terminal device, wherein
the image processing unit includes
a speed-lowering determination unit that determines, based on related information of the medical image, a setting item pertaining to a communication wait process for lowering a transmission timing from the medical image processing server to the terminal of a result of image processing, the related information of the medical image including at least disease information about whether a disease corresponding to the medical image is of a hyperacute phase, checkup information indicating which medical image pickup device captured the medical image, or supplementary information about an annotation on the medical image, the image operation input being a frame-by-frame playback operation that is input through the terminal device, the setting item being a frame transfer delay time in a frame-by-frame playback operation, and
a speed-lowering processing unit that carries out the communication wait process based on the setting item.

2. The medical image processing server according to claim 1, wherein:
based on the related information of the medical image, the communication wait process is performed.

3. The medical image processing server according to claim 2, wherein
depending on the number of pieces of supplementary information of the image, the communication wait process is performed.

4. A medical image information system comprising:
a terminal device that is connected via a network; and
a medical image processing server that carries out image processing based on a request from the terminal device and transmits a result thereof to the terminal device, wherein
the medical image processing server includes
a medical image storage unit in which a medical image is stored, and
an image processing unit that generates, from the medical image, a display screen and display screen information based on a request from the terminal device to transmit to the terminal device, and
the image processing unit includes
a speed-lowering determination unit that determines, based on either related information of a medical image or connection status of the terminal device or both, a setting item pertaining to a communication wait process for lowering a transmission timing from the medical image processing server to the terminal of a result of image processing, the related information of the medical image including at least disease information about whether a disease corresponding to the medical image is of a hyperacute phase, checkup information indicating which medical image pickup device captured the medical image, or supplementary information of an about an annotation on the medical image, the setting item being a frame transfer delay time in the frame-by-frame playback operation, and
a speed-lowering processing unit that carries out the communication wait process based on the setting item.

5. The medical image information system according to claim 4, wherein:
based on the related information of the medical image, the communication wait process is performed.

6. The medical image information system according to claim 4, wherein
when the connection status is a thin-client connection, the communication wait process is performed.

7. The medical image information system according to claim 6, wherein:
the image processing unit further includes a speed-lowering information acquisition unit; and the speed-lowering information acquisition unit acquires information at a time of communication connection which contains at least a bandwidth corresponding to the connection status, a delay, an image display condition, or monitor resolution, and the communication wait process is performed based on the information at the time of communication connection.

8. The medical image information system according to claim 1, wherein the related information of the medical image further includes an operational status of a user being an operation procedure of an image operation input that is input through the terminal device to indicate how quickly the frame-by-frame playback operation is to be performed.

9. The medical image information system according to claim 4, wherein the related information of the medical image further includes an operational status of a user being an operation procedure of an image operation input that is input through the terminal device to indicate how quickly the frame-by-frame playback operation is to be performed.

* * * * *